United States Patent
Stanek et al.

(10) Patent No.: US 6,458,280 B1
(45) Date of Patent: Oct. 1, 2002

(54) DEVICE AND METHOD FOR DISPENSING BACTERIOSTAT INTO HUMIDIFIER

(75) Inventors: Terrence L. Stanek, St. Charles, MO (US); Mark J. Tomasiak, St. Peters, MO (US); Steve Rhea, St. Peters, MO (US)

(73) Assignee: Emerson Electric Co., St. Louis, MO (US)

( * ) Notice: Subject to any disclaimer, the term of this patent is extended or adjusted under 35 U.S.C. 154(b) by 0 days.

(21) Appl. No.: 09/474,571

(22) Filed: Dec. 29, 1999

Related U.S. Application Data

(60) Provisional application No. 60/114,847, filed on Jan. 6, 1999.

(51) Int. Cl.[7] ................................................. C02F 1/50
(52) U.S. Cl. ................... 210/764; 210/744; 210/198.1; 222/64; 222/544; 422/28; 422/106
(58) Field of Search ................................. 210/744, 764, 210/198.1; 222/64, 544; 422/28, 106; 261/DIG. 4, DIG. 15, DIG. 46

(56) References Cited

U.S. PATENT DOCUMENTS

| | | | |
|---|---|---|---|
| 3,128,018 A | | 4/1964 | Corsette et al. ............. 222/585 |
| 3,237,571 A | | 3/1966 | Corsette ..................... 103/188 |
| 3,248,021 A | | 4/1966 | Corsette et al. ............. 222/321 |
| 3,361,078 A | | 1/1968 | Cooprider ................... 103/188 |
| 3,362,344 A | | 1/1968 | Duda ......................... 103/188 |
| 3,776,215 A | * | 12/1973 | Howard et al. |
| 3,949,906 A | | 4/1976 | Petersen et al. ............. 222/153 |
| 4,276,241 A | * | 6/1981 | Stewart et al. |
| 4,286,736 A | | 9/1981 | Corsette ..................... 222/321 |
| 4,340,158 A | | 7/1982 | Ford et al. .................. 222/321 |
| 4,369,899 A | | 1/1983 | Magers et al. ............... 222/153 |
| 4,375,266 A | | 3/1983 | Magers ...................... 222/321 |
| 4,479,589 A | | 10/1984 | Ford ......................... 222/153 |
| 4,512,501 A | | 4/1985 | Foster ....................... 222/153 |
| 4,524,888 A | | 6/1985 | Tada ......................... 222/153 |
| 4,663,091 A | * | 5/1987 | Seo |
| 5,016,780 A | | 5/1991 | Moretti ...................... 222/153 |
| 5,096,094 A | | 3/1992 | Guilbert ..................... 222/153 |
| 5,219,098 A | | 6/1993 | Tada ......................... 222/153 |
| 5,222,632 A | | 6/1993 | Tada ......................... 222/153 |
| 5,329,939 A | * | 7/1994 | Howe |
| 5,520,854 A | * | 5/1996 | Porco et al. |
| 5,524,793 A | | 6/1996 | O'Neill .................. 222/153.13 |
| 5,664,730 A | * | 9/1997 | Vallieres et al. |
| 5,859,952 A | * | 1/1999 | Levine et al. |
| 6,093,422 A | * | 7/2000 | Denkewicz, Jr. et al. |

FOREIGN PATENT DOCUMENTS

| | | | |
|---|---|---|---|
| JP | 60-166769 | 8/1985 | ............. F04B/9/14 |
| JP | 4-267757 | 9/1992 | ........... B65D/47/34 |

\* cited by examiner

*Primary Examiner*—Betsey Morrison Hoey
(74) *Attorney, Agent, or Firm*—Howrey Simon Arnold & White, LLP

(57) ABSTRACT

A humidifier with an integrated bacteriostat dispenser is disclosed. In one embodiment, a hand-operated bacteriostat pump is mounted on the humidifier housing and dispenses a predetermined amount of bacteriostat into the water tray of the humidifier when operated upon. In another embodiment, the bacteriostat automatically dispenses an amount of bacteriostat appropriate for the amount of water discharged from a water bottle into the water tray. In this embodiment, a chamber is defined for holding bacteriostat. A regulator keeps the amount of bacteriostat in the chamber at a predetermined level. A plunger head is partially disposed in the chamber and is connected to a surface the position of which changes with the water level in the water bottle. The position of the plunger head thus moves as the water level in the water bottle changes, displacing bacteriostat into the water tray. In another embodiment, a method for dispensing bacteriostat into a humidifier is disclosed. According to this method, an amount of bacteriostat proportional to the amount of water discharged from a water bottle into a water tray in a humidifier is dispensed into the water tray at substantially the same time as the water is discharged.

15 Claims, 3 Drawing Sheets

DEVICE AND METHOD FOR DISPENSING BACTERIOSTAT INTO HUMIDIFIER

CROSS-REFERENCE TO RELATED APPLICATION

This application claims the benefit of U.S. Provisional Application No. 60/114,847, entitled "Device And Method For Dispensing Bacteriostat Into A Humidifier," filed Jan. 6, 1999, by the same inventors, which is incorporated herein by reference in its entirety.

BACKGROUND OF THE INVENTION

1. Field of the Invention

The present invention relates generally to humidifiers, and, more particularly, to a device and method for dispensing bacteriostat into a humidifier.

2. Description of the Related Art

Humidifiers are commonly used in homes to add moisture to the air, particularly during the winter months, when the air typically has low moisture content. The added more content in the air during these dry, cold weather months provides for a more comfortable environment within the home. As a result, humidifiers have become a popular, inexpensive means for achieving optimal air moisture content within the home environment.

A humidifier typically includes a water tray for holding water and a moisture source, such as a wick, adapted to draw water from the water tray and disperse the water drawn from the water tray. To prevent bacterial growth in and near the water tray, bacteriostat may be added to the water. For example, certain types of bacteriostat approved by the United States Environmental Protection Agency may be used for this purpose.

Common difficulties in using a bacteriostat include the inconvenience of application and the inability to apply an amount of bacteriostat appropriate for the amount of water in the water tray. Typically, the user must retrieve the container of the bacteriostat from a location at a distance from the humidifier, measure an appropriate amount of bacteriostat from the container, and dispense the measured bacteriostat into the water tray. Because the amount of water in the water tray is often not precisely known, it is difficult in many cases to estimate how much bacteriostat to apply. Application of insufficient amount of bacteriostat reduces the effectiveness of the water treatment. Over-application, as is frequently the case, results in waste.

The present invention is directed to alleviating one or more of the aforementioned problems.

SUMMARY OF THE INVENTION

In one aspect of the present invention, a humidifier includes a manual bacteriostat dispenser, located within the humidifier housing. The dispenser dispenses substantially a fixed amount of bacteriostat each time the user activates the dispenser.

In another aspect of the present invention, a humidifier includes a water storage device and an automatic bacteriostat dispenser, which automatically dispenses bacteriostat as water is added to the water tray from the water storage device. The position of a surface moves in accordance with the water level in the water storage device. A plunger assembly is in contact with, and moves with, the surface and has a plunger head partially disposed within a chamber filled with bacteriostat. The movement of the plunger displaces bacteriostat out of the chamber and into the water tray.

In another aspect of the present invention, a method of dispensing bacteriostat is disclosed, wherein as water is discharged into the water tray, an amount of bacteriostat substantially proportional to the amount of water discharged is dispensed into the water tray at substantially the same time as water is discharged into the water tray.

In another aspect of the present invention, a method of dispensing bacteriostat is disclosed, wherein the actuator head of a piston pump is depressed a predetermined number of times each time the water storage device is filled.

BRIEF DESCRIPTION OF THE DRAWINGS

Other objects and advantages of the invention will become apparent upon reading the following detailed description and upon reference to the drawings in which.

Figure 1A:
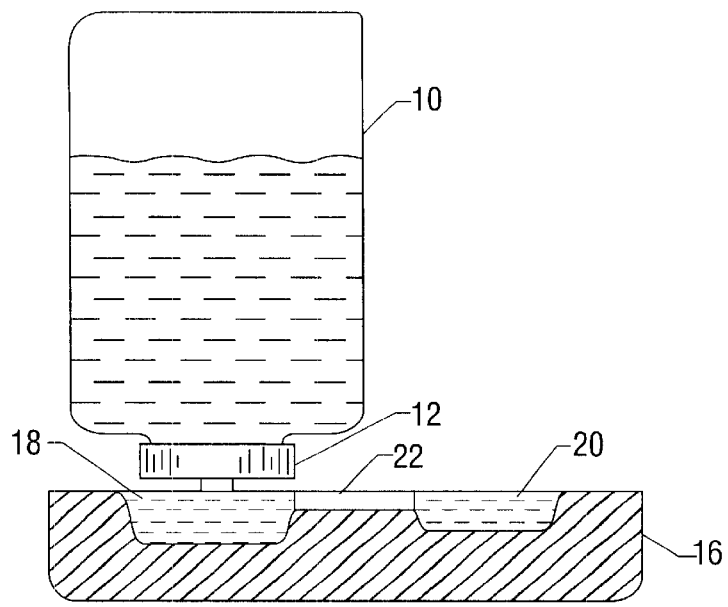
FIGS. 1A and 1B show a portion of a first embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nonetheless be a routine undertaking for those of ordinary skill in the art having the benefit of this disclosure.

Figure 1B:
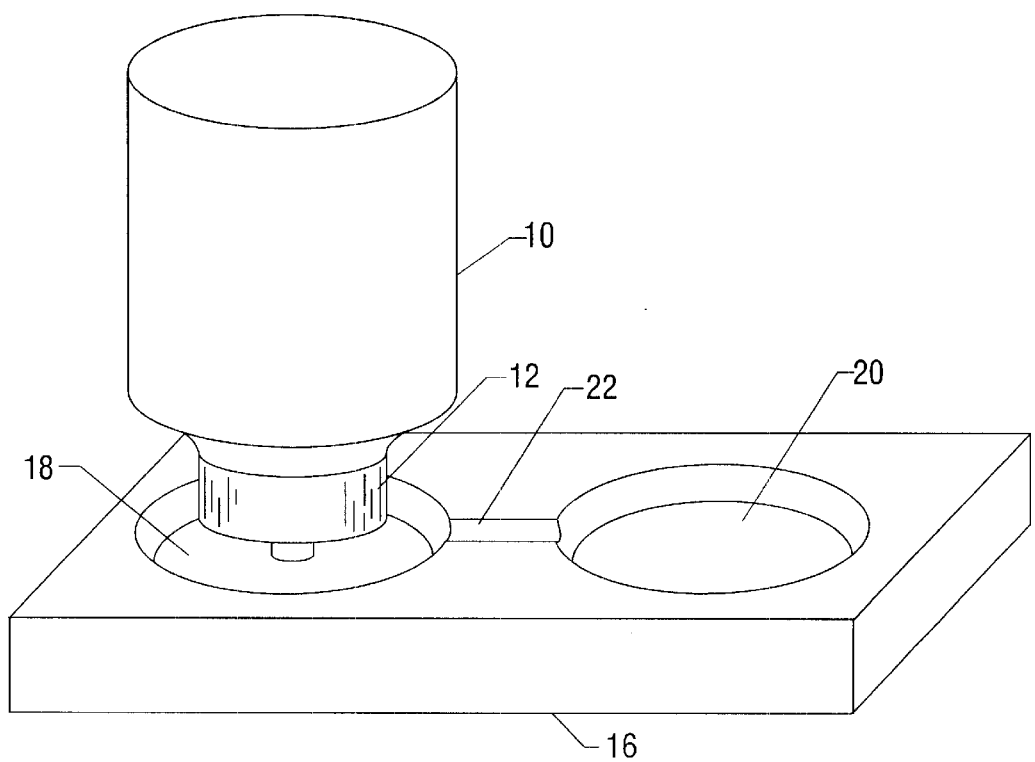

Referring to FIGS. 1A and 1B, a first embodiment of the present invention includes a bacteriostat bottle 10, a downwardly pointing dispensing cap 12 mounted on the bottom surface of the bacteriostat bottle 10, and a bacteriostat receptacle 16. Two chambers 18 and 20 are defined on the receptacle 16 and are interconnected by a channel 22 so that the bacteriostat levels in both chambers 18 and 20 are the same. The dispensing cap 12 is positioned directly above the first chamber 18 at a height that the level of bacteriostat in the first chamber 18 may reach. The dispensing cap 12 dispenses bacteriostat into the second chamber 20 via the first chamber 18 and channel 22 when the level of bacteriostat in the first chamber 18 is below the dispensing cap 12. The dispensing cap stops dispensing bacteriostat when the level of bacteriostat in the first chamber 18 reaches the dispensing cap 12. The dispensing cap 12 and the first chamber 18 effectively form a regulator that regulates the bacteriostat level in the second chamber 20.

Figure 2:
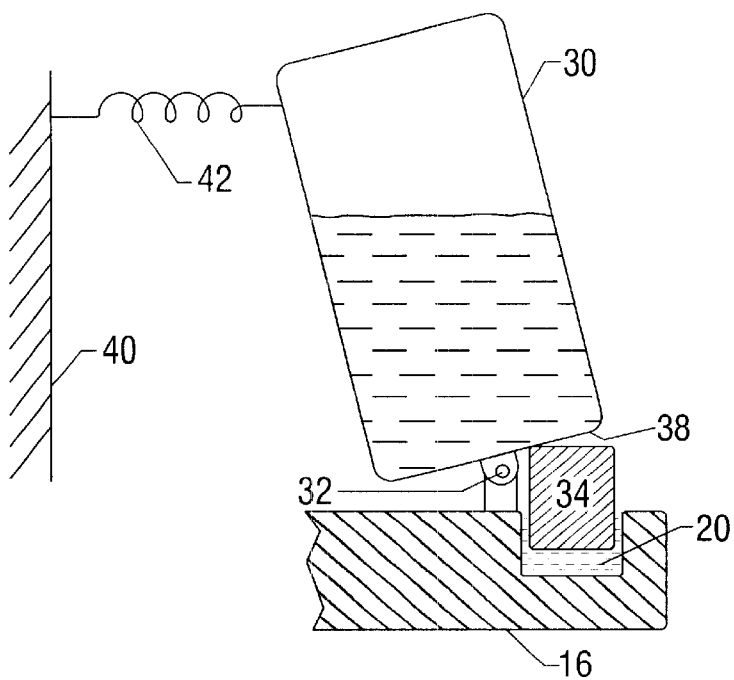
FIG. 2 shows another portion of a first embodiment of the present invention.

Referring to FIG. 2, the embodiment also includes a water storage device such as a water bottle 30, which supplies water to a water tray (not shown) in the humidifier. The water bottle 30 is pivotally supported at the bottom by a pivot point 32. A biasing device, such as a spring 42 extending from the humidifier wall 40, is in contact with the water bottle 30 and exerts a horizontal force that tends to tilt the water bottle away from the wall 40. The location of the pivot point 32 relative to the water bottle 30 is chosen such that the weight of the water in the water bottle 30 tends to cause the water bottle 30 to tilt towards the wall 40. Accordingly, the torque about the pivot point 32 exerted on the water bottle 30 by the spring 42 is opposite the torque about the pivot point 32 exerted by gravity. When the water bottle is full, the weight of the water causes the water bottle to tilt a maximum amount toward the wall 40. As water is discharged from the water bottle 30 into the water tray, the water bottle 30 becomes lighter and is pushed back towards a vertical position by the spring 42.

A portion 38 of the bottom surface of the water bottle 30 is positioned above the second bacteriostat receptacle chamber 20, as shown in FIG. 2. A plunger head 34 is partially disposed within the second chamber 20 and is in contact with the portion 38 of the bottom surface of the water bottle 30. The plunger head 34 in this case floats in the bacteriostat and is held in contact with the bottom of the water bottle 30 by buoyancy. The contact may also be made by attaching the plunger 34 to the portion 38 of the bottom surface.

In operation, when the water bottle 30 is full, it is positioned at its maximum tilt angle toward the humidifier wall 40. The clearance between the bottom surface of the water bottle 30 and the second receptacle chamber 20 is at its maximum If the level of bacteriostat in the second receptacle chamber 20 is below the dispensing cap 12, the dispensing cap 12 will dispense bacteriostat from the bacteriostat bottle 10 into the first and second receptacle chambers 18 and 20 until the level of bacteriostat in the receptacle chambers 18 and 20 reaches the dispensing cap 12.

As water is dispensed into the humidifier from the water bottle 30, the water bottle 30 is pushed back towards the vertical position by the spring 42. As a result, the plunger 34 is pushed into, and displaces a portion of, the bacteriostat in the second receptacle chamber 20. The displaced bacteriostat overflows the receptacle chambers 18 and 20 into the water tray. The angular displacement (i.e., the tilt) of the water bottle 30 is substantially proportional to the amount of water contained therein. Accordingly, an amount of bacteriostat substantially proportional to the amount of water discharged from the water bottle 30 into the water tray is automatically dispensed into the water tray at substantially the same time as water is discharged into the water tray from the water bottle 30.

When the water bottle 30 is refilled, it returns to the position of maximum angular displacement from vertical, freeing the plunger 34 to rise and thereby displaying less bacteriostat. The levels of bacteriostat in the receptacle chambers 20 and 18 decrease as a result, causing the bacteriostat bottle 10 to dispense bacteriostat tiff the levels in the chambers 20 and 18 are again at the dispensing cap 12. The process described above is then repeated.

Figure 3:
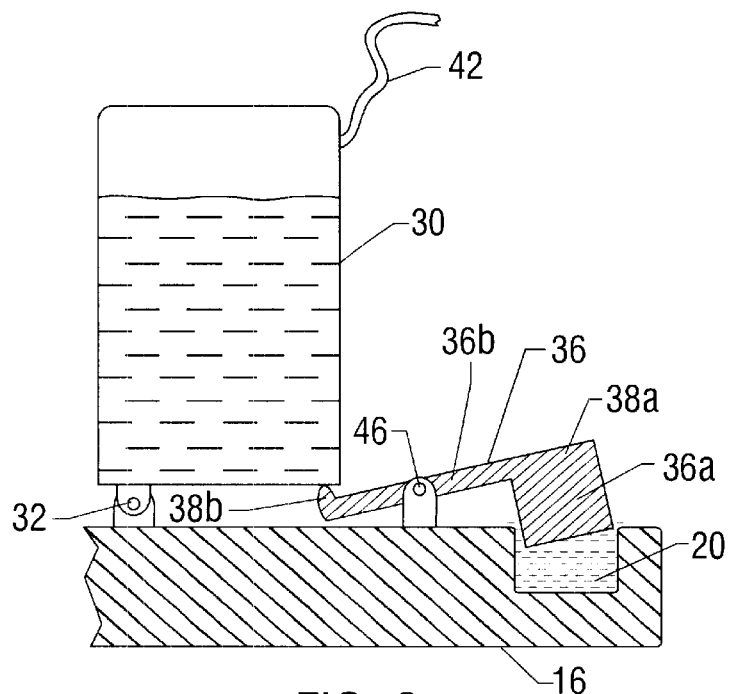
FIG. 3 shows a second embodiment of the present invention.

In a second embodiment, illustrated in FIG. 3, the relation between the weight of the water bottle 10 and the direction of the angular displacement of the water bottle 10 is reversed from that in the first embodiment. A biasing device, such as a spring 42, tends to push the water bottle 30 from a vertical position to a tilted position. The pivot point 32 is positioned so that the water bottle 30 tilts towards, thereby compressing, a spring 42 as the weight of the water bottle 30 increases. The water bottle 30 is positioned laterally away from the second bacteriostat receptacle chamber 20. A plunger assembly 36 has a plunger head 36a, which has a higher specific gravity than the bacteriostat used and is in vertical alignment with, and partially disposed within, the second bacteriostat receptacle chamber 20, and a lever 36b, which has a first end 38a connected to the plunger head 36a and a second end 38b positioned under the water bottle 30. The lever 36b is pivotally supported by lever pivot point 46 located between two ends 38a and 38b of the lever 36b.

In operation, when the water bottle 30 is full, it is in an upright or vertical position, pressing down on the second end 38b of the lever 36b, thereby raising the plunger head 36a to its highest position. Bacteriostat is dispensed into the chambers 18 and 20 as described above. As water is dispensed into the humidifier from the water bottle 30, the water bottle 30 is pushed away from the vertical position by the spring 42. The second end 38b of the lever 36b rises, and the plunger head 36a falls deeper into the bacteriostat, thereby displacing a portion of the bacteriostat in the second receptacle chamber 20. The displaced bacteriostat overflows the receptacle chambers 18 and 20 into the water tray.

Figure 4:
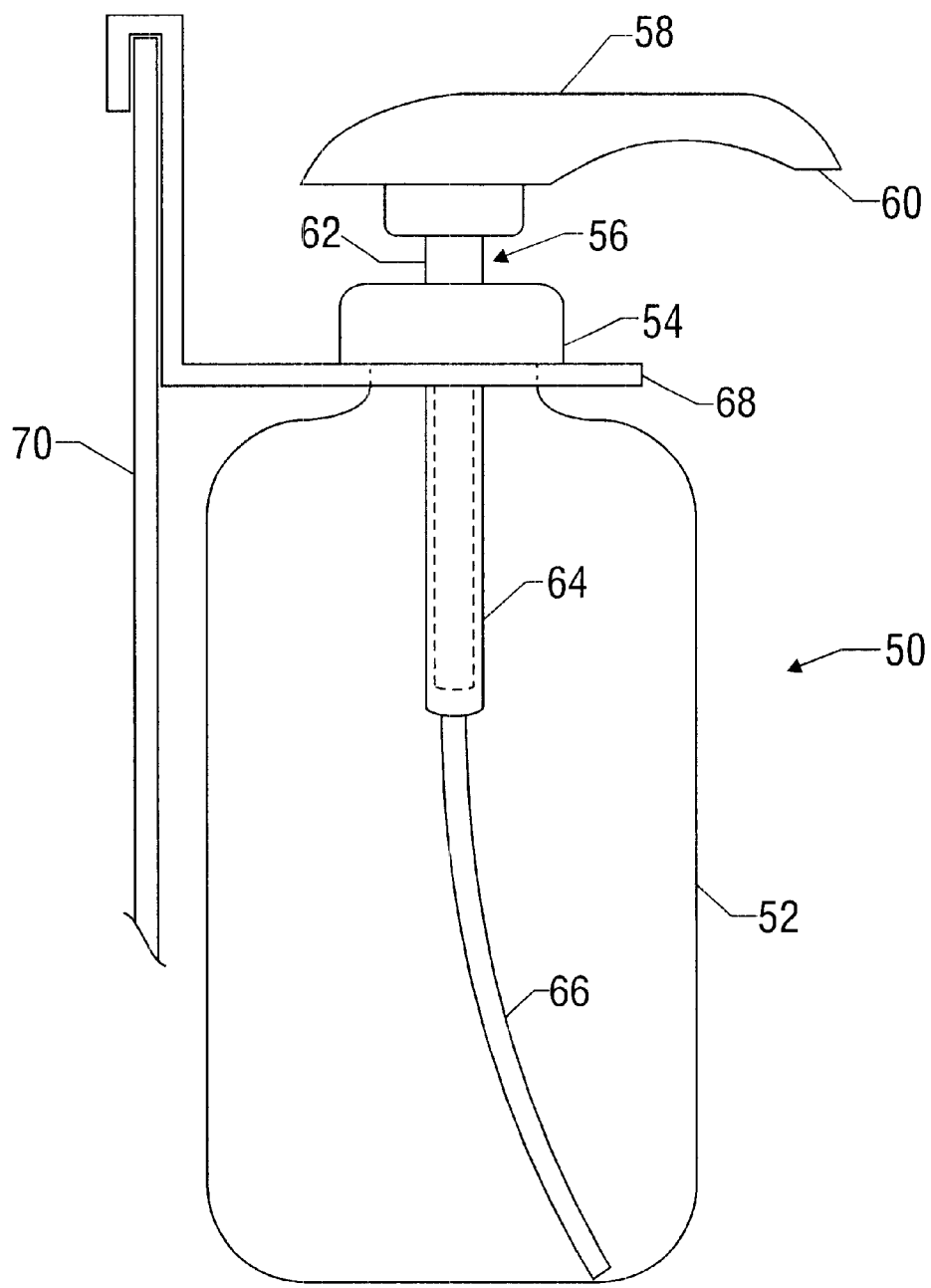
FIGS. 4 shows a third embodiment of the present invention.

In a third embodiment, illustrated in FIG. 4, a bacteriostat dispenser 50 is suspended within the humidifier housing 70. The bacteriostat dispenser 50 includes a storage bottle 52, a cap 54 and a liquid dispensing pump 56. The storage bottle 52 is secured to a mounting bracket 68, which is attached to the humidifier housing 70. The liquid dispensing pump 56 is a piston pump of a type commonly used for dispensing lotions, liquid soaps or creams and includes an actuator head 58 mounted on a piston 62, which is mounted for reciprocating motion in an accumulator 64, which is mounted on the cap 54 and positioned inside the storage bottle 52. The bottom end of the accumulator 64 is connected to a dip tube 66, which extends to the bottom of the storage bottle 52. The actuator head 58 includes a dispensing nozzle 60, which is positioned above the water tray. As the actuator head 58 is pushed from its highest position to its lowest position, a fixed amount of bacteriostat is pumped through the dispensing nozzle into the water tray below. After the actuator head 58 is released, it is returned to its highest position by a compression spring (not shown) inside the pump housing 64. By pushing the actuator from its highest position to its lowest position a predetermined number of times each time the humidifier is refilled with water, an accurate and appropriate amount of bacteriostat is added to the water.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the clams below.

What is claim is:

1. A humidifier comprising:
   a water tray;
   a moisture source adapted to draw water from said water tray and disperse the water drawn from said water tray;
   a bottle for containing a volume of bacteriostat and having an outlet; and a bacteriostat dispenser providing communication between said outlet and said water tray and adapted to dispense into said water tray an amount of bacteriostat substantially proportional to the amount of water added to said water tray.

2. The humidifier as set forth in claim 1, wherein said bacteriostat dispenser is a liquid dispensing pump.

3. The humidifier as set forth in claim 2, wherein said liquid dispensing pump is a piston pump.

4. The humidifier as set forth in claim 1, wherein said bacteriostat dispenser is a valve.

5. A humidifier, comprising:
a water tray;
a moisture source adapted to draw water from said water tray and disperse the water drawn front said water tray;
a bottle for containing a volume of bacteriostat and having an outlet; and
a bacteriostat dispenser providing communication between said outlet and said water tray and adapted to dispense a fixed amount of bacteriostat from said bottle into said water tray;
wherein said bacteriostat dispenser includes an actuator head for pumping the fixed amount of bacteriostat through said bacteriostat dispenser when the actuator head is pushed from its highest position to its lowest position.

6. A bacteriostat dispensing assembly for a humidifier having a water storage device, said dispensing assembly comprising:
a bacteriostat container;
a receptacle defining a chamber therein for receiving bacteriostat from said bacteriostat container;
a regulator in fluid communication with said bacteriostat container and adapted to discharge bacteriostat into said chamber and maintain the level of bacteriostat in said chamber;
a surface, the position of said surface being indicative of the water level in the water storage device;
a plunger assembly in contact with said surface and comprising a plunger head for displacing bacteriostat in said chamber, said plunger head being at least partially disposed within said chamber, whereby the position of said plunger head changes in response to the water level change in the water storage device, thereby changing the amount of bacteriostat displaced.

7. The bacteriostat dispensing assembly as set forth in claim 6, wherein said regulator comprises:
a downwardly-pointing nozzle;
a receptacle chamber positioned below said nozzle such that said nozzle is reachable by the surface of bacteriostat in said chamber.

8. The bacteriostat dispensing assembly as set forth in claim 7, further comprising:
a pivot point for pivotally supporting the water storage device; and
a biasing element exerting a torque about said pivot point on the water storage device opposite the torque about said pivot point exerted by gravity on the water storage device.

9. The bacteriostat dispensing assembly as set forth in claim 8, wherein said surface comprises a portion of the water storage device.

10. The bacteriostat dispensing assembly as set forth in claim 9, wherein said plunger assembly further comprises a lever having a first end and a second end, said first end being attached to said plunger head, and said second end being in contact with said surface, said bacteriostat dispensing assembly further comprising a lever pivot point for pivotally supporting said lever.

11. The bacteriostat dispensing assembly as set forth in claim 8, wherein said plunger assembly further comprises a lever having a first end and a second end, said first end being attached to said plunger head, and said second end being in contact with said surface, said bacteriostat dispensing assembly further comprising a lever pivot point for pivotally supporting said lever.

12. The bacteriostat dispensing assembly as set forth in claim 7, wherein said plunger assembly further comprises a lever having a first end and a second end, said first end being attached to said plunger head, and said second end being in contact with said surface, said bacteriostat dispensing assembly further comprising a lever pivot point for pivotally supporting said lever.

13. A method of adding bacteriostat to a water tray in a humidifier having a water storage device that discharges water into said water tray, said method comprising the step of dispensing bacteriostat into said water tray at substantially the same time as water is discharged into said tray from said water storage device, the amount of the bacteriostat dispensed being substantially proportional to the amount of water discharged from said water storage device to said water tray.

14. The method as set forth in claim 13, wherein the step of dispensing bacteriostat comprises:
dispensing bacteriostat into a chamber;
maintaining the level of bacteriostat in said chamber;
displacing an amount of bacteriostat out of said chamber and into said water tray in accordance with the water level in said water storage device.

15. A humidifier, comprising:
a water tray;
a moisture source adapted to draw water from said water tray and disperse the water drawn from said water tray,
a bottle for containing a volume of bacteriostat and having an outlet;
a bacteriostat dispenser having a chamber, and providing communication between said chamber and said bottle outlet, wherein said bacteriostat dispenser includes an actuator head for pumping the fixed amount of bacteriostat through said bacteriostat dispenser when the actuator head is pushed from its highest position to its lowest position.

* * * * *

UNITED STATES PATENT AND TRADEMARK OFFICE
CERTIFICATE OF CORRECTION

PATENT NO.     : 6,458,280 B1                                           Page 1 of 1
DATED          : October 1, 2002
INVENTOR(S)    : Terence L. Stanek et al.

It is certified that error appears in the above-identified patent and that said Letters Patent is hereby corrected as shown below:

Column 5,
Line 15, delete the word "front" and add -- from --

Signed and Sealed this

Eighteenth Day of March, 2003

JAMES E. ROGAN
*Director of the United States Patent and Trademark Office*